United States Patent
Wang et al.

(10) Patent No.: US 11,479,519 B2
(45) Date of Patent: Oct. 25, 2022

(54) METHOD FOR AROMATIZATION OF LIGHT ALKANES

(71) Applicants: China Energy Investment Corporation Limited, Beijing (CN); National Institute of Clean-and-Low-Carbon Energy, Beijing (CN)

(72) Inventors: Hui Wang, Mountain View, CA (US); Yizhi Xiang, Mountain View, CA (US); John Matsubu, Mountain View, CA (US); Junjun Shan, Mountain View, CA (US); Jihong Cheng, Mountain View, CA (US); Qi Sun, Beijing (CN); Lisa Nguyen, Mountain View, CA (US)

(73) Assignee: CHINA ENERGY INVESTMENT CORPORATION LIMITED, Beijing (CN)

(*) Notice: Subject to any disclaimer, the term of this patent is extended or adjusted under 35 U.S.C. 154(b) by 0 days.

(21) Appl. No.: 16/728,654

(22) Filed: Dec. 27, 2019

(65) Prior Publication Data
US 2020/0207683 A1 Jul. 2, 2020

(30) Foreign Application Priority Data
Dec. 29, 2018 (CN) .......................... 201811643291.0

(51) Int. Cl.
C07C 2/76 (2006.01)
B01J 37/00 (2006.01)
(Continued)

(52) U.S. Cl.
CPC ............. *C07C 2/76* (2013.01); *B01J 37/0009* (2013.01); *B01J 37/30* (2013.01); *C07C 15/04* (2013.01); *C07C 2523/42* (2013.01)

(58) Field of Classification Search
None
See application file for complete search history.

(56) References Cited

U.S. PATENT DOCUMENTS 3,775,502 A * 11/1973 Oishi ....................... B01J 29/12
585/419
4,964,975 A * 10/1990 Chao ...................... B01J 23/622
208/139

(Continued)

FOREIGN PATENT DOCUMENTS

| CN | 103313959 A | 9/2013 |
| WO | 12078511 A2 | 6/2012 |

*Primary Examiner* — Philip Y Louie
*Assistant Examiner* — Alyssa L Cepluch
(74) *Attorney, Agent, or Firm* — Calfee, Halter & Griswold LLP

(57) ABSTRACT

A method for aromatization of light alkanes, comprising: subjecting the light alkanes to dehydroaromatization reaction in the presence of aromatization catalysts including carriers and metal active components supported on the carriers, the metal active components include platinum, the carriers include zeolites and binders, and at least 80 wt. % of the metal active components are distributed on the zeolites. The method of the present disclosure may increase yield of the target product—aromatic hydrocarbons, and the regenerated catalyst can still maintain high catalytic performance. In addition, the method of the present disclosure can meet the requirements of industrial applications.

23 Claims, 1 Drawing Sheet

(51) Int. Cl.
*B01J 37/30* (2006.01)
*C07C 15/04* (2006.01)

(56) References Cited

U.S. PATENT DOCUMENTS

| | | |
|---|---|---|
| 8,946,107 B2 | 2/2015 | Lauritzen et al. |
| 9,144,790 B2 | 9/2015 | Lauritzen et al. |
| 2010/0048969 A1* | 2/2010 | Lauritzen ............... C10G 11/05 585/417 |
| 2018/0194701 A1* | 7/2018 | Hong ........................ C07C 2/46 |

* cited by examiner

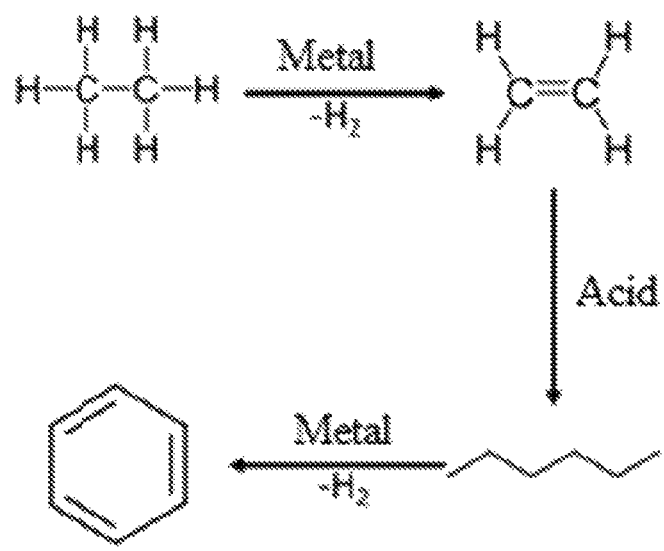

METHOD FOR AROMATIZATION OF LIGHT ALKANES

PRIORITY CLAIM & CROSS REFERENCE

The application claims priority to Chinese Application No. 201811643291.0, filed on Dec. 29, 2018, entitled "Method For Aromatization Of Light Alkanes", which is herein specifically and entirely incorporated by reference.

FIELD OF THE INVENTION

The present disclosure relates to the technical field of producing aromatic hydrocarbons from light alkanes, and particularly to a method for aromatization of light alkanes.

BACKGROUND OF THE INVENTION

During the dehydroaromatization process of ethane, the ethane can be selectively converted into high-value Benzene-Toluene-Xylene (BTX) products directly in the presence of a catalyst. Because of the low reactivity of ethane, the reaction temperature shall be set at least 600° C. generally, which causes severe coking of the catalyst. Therefore, the catalyst used in the dehydroaromatization reaction must be regenerable from an economical perspective.

FIG. 1 illustrates the main process of dehydroaromatization of ethane in the presence of a supported metal catalyst: 1) the ethane is activated at the metal site of the catalyst and converted to ethylene; 2) the ethylene is activated at the acid site of the catalyst and converted into C6+ hydrocarbons; 3) the C6+ hydrocarbons are dehydrocyclized at the metal site to form aromatic compounds. As can be seen, the proximity between the metal and the acid site is vital for improving selectivity of aromatic hydrocarbons. Otherwise, the ethylene is prone to be excessively oligomerized and converted into heavier hydrocarbons prior to the cyclization, it will not only reduce selectivity of aromatic hydrocarbons, but also cause the formation of more coke, which results in quick deactivation of the catalyst.

The typical noble metal catalyst, supported on zeolite, is used for catalyzing the dehydroaromatization of ethane. This catalyst usually contains 0.02-0.2% of the supported metal. For the sake of facilitating the industrial application, it is necessary to combine the zeolite powder with a binder being capable of providing mechanical strength to form the catalyst particles, thereby reducing the pressure drop of catalyst bed.

Example 1 of U.S. Pat. No. 8,946,107B2 discloses a binder-free dehydroaromatization catalyst. Specifically, the active components such as platinum (Pt) are deposited on ZSM-5 powder, and the powder is then loaded into a plastic bag and pressed using an isostatic press, subsequently crushing and sieving the powder to obtain catalyst particles. However, the catalyst has poor mechanical strength and cannot be used industrially.

U.S. Pat. No. 9,144,790B2 discloses a catalyst that uses gallium (Ga) as a second metal of the catalyst to suppress undesirable catalytic activity of Pt to improve selectivity and a method for preparing the same. The method comprises mixing ZSM-5 zeolite powder with alumina and extruding the mixture to obtain an extrudate; subsequently depositing the active components such as Pt in pores of the extrudate. A binder is used for bonding individual zeolite crystal particles to keep the catalyst particle size within the optimum range for fluidized bed operations or to prevent the excessive pressure drop of the catalyst particle during operations of fixing or moving the fluidized bed.

SUMMARY OF THE INVENTION

The inventors of the present invention have discovered that when a binder and a zeolite are present simultaneously in the catalyst used in the dehydroaromatization reaction of the light alkanes, the active components such as Pt, will be deposited on the binder in addition to the zeolite; if a portion of Pt is deposited on the binder, it will result in the reduced activity of the catalyst and low selectivity of the aromatic hydrocarbons; moreover, the Pt on the binder can be easily sintered at high temperature (for example, during the process of reaction or catalyst regeneration), thus the regenerated catalyst cannot be restored to its original activity. The present invention is proposed in order to solve the aforementioned problems.

The present disclosure provides a method for aromatization of light alkanes, comprising: subjecting the light alkanes to dehydroaromatization reaction in the presence of aromatization catalysts including carriers and metal active components supported on the carriers, the metal active components include platinum (Pt), the carriers include zeolites and binders, and at least 80 wt. % of the metal active components are distributed on the zeolites.

Compared with the existing dehydroaromatization reaction, the catalyst applied by the method of the present disclosure has higher catalytic activity in dehydroaromatization and can improve selectivity of the reaction product BTX, and the regenerated catalyst shares comparative performance with the original catalyst, that is, the catalyst has the characteristics of high regenerability. In addition, the method of the present disclosure can on one hand minimize the amount of Pt on the binder by adjusting the Pt distribution and minimizing the Pt supporting on the catalyst, and on the other hand, the second active component (such as Ga) can be omitted. Even if only a small amount of Pt is present, the catalytic activity of the catalyst and the selectivity of the product BTX can be ensured, thereby the cost of the catalyst is reduced.

BRIEF DESCRIPTION OF THE DRAWINGS

FIG. 1 is a schematic diagram of producing aromatic compounds by dehydroaromatization of ethane.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

The present disclosure provides a method for aromatization of light alkanes, comprising: subjecting the light alkanes to dehydroaromatization reaction in the presence of aromatization catalysts including carriers and metal active components supported on the carriers, the metal active components include platinum (Pt), the carriers include zeolites and binders, and at least 80 wt. % (80 wt. %, 85 wt. %, 90 wt. %, 95 wt. %, 100 wt. % or any content therebetween) of the metal active components are distributed on the zeolites.

In the present disclosure, the proportion of the metal active components distributed on the zeolites may be derived from an elemental mapping determined by transmission electron microscopy (STEM elemental mapping).

The metal active component in the present disclosure includes platinum (Pt), and the content of platinum may be selected within a relatively large range by referring to an existing aromatization catalyst. Generally, the content of platinum in the aromatization catalyst may be 100-10,000 ppm based on the total weight of the aromatization catalyst. In regard to the present disclosure, since the metal active component is mainly located on the zeolite portion of the carrier, a small amount of active components can ensure that the catalyst has higher catalytic performance, BTX selectivity and regenerability, the content of platinum is preferably within a range of 100-1,000 ppm, more preferably 200-1,000 ppm. In the present disclosure, unit "ppm" refer to "weight parts per million", 1 ppm=0.001 wt. %.

Although the aromatization catalyst in the present disclosure may produce desirable effects of the present invention by only containing a small amount of Pt, the metal active component is not limited to Pt, it may include other metals conventionally used as the aromatization catalyst, for example, at least one selected from the group consisting of Fe, Cu, Co, Sn, Zn, Mn, Ni, Ga, Bi, La and Ce. According to a preferred embodiment, the content of the metal active component is 100-1,000 ppm, such as 200 ppm, 300 ppm, 400 ppm, 500 ppm, 550 ppm, 600 ppm, 700 ppm, 800 ppm, 900 ppm, 1,000 ppm or any content therebetween.

In the present disclosure, the zeolite may be one or two or more selected from the group consisting of MFI, MEL, MTW, MOR, BEA, TMN and IMF zeolites, and is preferably ZSM-5 zeolite. Generally, the silica-alumina ratio (i.e., the molar ratio between silica and alumina) of the zeolite may be within a range of 20-100, such as 20, 30, 35, 40, 50, 60, 70, 80, 90, 100 or any ratio therebetween.

It is preferable in the present disclosure that the ratio of P1 (the weight percentage of the metal active components distributed on the zeolites based on the total amount of the metal active components) and P2 (the weight percentage of the zeolites in the carriers) is higher than 1.1, such as 1.11, 1.15, 1.2, 1.25, 1.28, 1.29, 1.3, 1.5 or any value therebetween.

The type and content of the binder in the present disclosure may be selected with reference to the prior art, as long as the catalyst can be molded. The content of the binder may be 10-50 wt. %, preferably 15-40 wt. %, based on the total weight of the aromatization catalyst. The content of the binder in the present disclosure is determined according to the amount of the inputted materials.

The present disclosure does not impose a specific limitation in regard to the shape of the aromatization catalyst, it may be selected with reference to the prior art. For example, the shape of the aromatization catalyst may be spherical, cylindrical, stripe-type or irregular particles.

In one embodiment, the binder is one or two or more selected from the group consisting of alumina, lanthanum oxide, cerium oxide, zirconia and titanium dioxide. In this embodiment, the aromatization catalyst is prepared with a method including the following steps (hereinafter referred to as "Method 1"):

1) Molding

Mixing the zeolite with the binder, molding and calcinating the resulted mixture;

2) Supporting (Ion Exchange Method)

Depositing ions of the metal active components on the calcinated product obtained in step 1) by an ion exchange method, and then drying and calcinating the resulted product. The drying process may be performed in the air, the drying temperature may be 70-95° C., and the drying time may be within a range of 6-30 hours.

In Method 1, step 2) may include: mixing and stirring the solution of compounds containing the metal active components with the calcinated product, and then sequentially performing solid-liquid separation, washing (e.g., with water) and drying; the volumetric ratio of the solution and the calcinated product is within a range of 1-50:1, the temperature of stirring is 15-95° C., and the time of stirring is 0.5-10 hours.

Optionally, in a case where the selected zeolite does not belong to H-type or $NH_4$-type zeolite, the ion exchange method further includes: prior to performing the depositing process, initially subjecting the calcinating product obtained in step 1) to an ion exchange with $NH_4Cl$ aqueous solution having a concentration of 1-5wt. % at a temperature of 60-95° C. for 1-5 hours.

In another preferred embodiment, the binder is one or two or more selected from the group consisting of silicon dioxide, aluminum phosphate and silicon carbide. In this embodiment, the aromatization catalyst is prepared by a method including the following steps (hereinafter referred to as "Method 2"):

1) Molding

Mixing the zeolite with the binder, molding and calcinating the resulted mixture;

2) Supporting (Impregnation Method or Ion Exchange Method)

Supporting the metal active components on the calcinated products obtained in step 1) by an impregnation method or an ion exchange method.

In yet another embodiment, the aromatization catalyst may be prepared by a method including the following steps (hereinafter referred to as "Method 3"):

1) Supporting (Impregnation Method or Ion Exchange Method)

Supporting the metal active components on the zeolites by an impregnation method or an ion exchange method;

2) Molding

Mixing the product obtained in step 1) with the binder, molding and calcinating the resulted mixture.

In Method 2 and Method 3, the impregnation method may comprise impregnating the calcinated product (Method 2) or zeolite (Method 3) with a solution of compounds containing the metal active components, and then drying and calcinating the obtained mixture. The drying process in the impregnation method may be implemented by means of evaporation (rotary evaporation), and the temperature may be within a range of 60-90° C. The specific operating conditions of the impregnation method are well-known in the art, and will not be repeated in the present disclosure.

In Method 2 and Method 3, the ion exchange may be performed with reference to Method 1, that is, mixing and stirring the solution of compounds containing the metal active components with the calcinated products (Method 2) or zeolites (Method 3), and sequentially performing the solid-liquid separation, washing (e.g., with water) and drying; the volumetric ratio of the solution to the calcinated products or zeolites is within a range of 1-50:1, the temperature of stirring is 15-95° C., and the time of stirring is 0.5-10 hours. Optionally, the ion exchange method further includes above-mentioned step of performing ion exchange of the calcinated products or zeolites with an ion exchange material.

The embodiment of Method 3 does not impose a special restriction on the binder, for example, the binder may be one or more of the binders listed in the two embodiments (i.e., Method 1 and Method 2).

Compounds containing metal active components comprise platinum-containing compound. Among the compounds containing metal active components in the present disclosure, the non-limiting examples of the platinum-containing compound include one or two or more selected from the group consisting of platinum hydroxide, chloroplatinic acid, platinum nitrate and platinum acetate. In a solution of the platinum-containing compound, the concentration of the platinum-containing compound may be 0.001-10 wt. %, preferably 0.05-5 wt. %. The solution generally refers to an aqueous solution.

In the three methods mentioned above for preparing a catalyst, the calcinating temperature of each step may be within a range of 300-600° C., and the calcinating time may be within a range of 1-5 hours.

In the three methods mentioned above for preparing a catalyst, the molding method may be selected with reference to an existing catalyst molding process, for example, the molding process is selected from extrusion molding and pelleting molding. The specific operation thereof is well-known in the art, and will not be repeated here.

According to the method for aromatization of light alkanes of the present disclosure, the light alkanes may be C2-C6 alkanes. Specifically, the light alkanes may be one or more selected from the group consisting of ethane, propane, n-butane, iso-butane, n-pentane, 2-methylbutane, 2,2-dimethyl propane, n-hexane, 2-methylpentane, 3-methylpentane, 2,3-dimethyl butane and 2,2-dimethyl butane. Preferably, the light alkane is ethane.

The method for aromatization of light alkanes of the present disclosure serves to illustrate the application of the aromatization catalyst in an aromatization reaction of the light alkanes, thus the conditions for dehydroaromatization reaction of the light alkanes are not particularly defined. The conditions for dehydroaromatization reaction may include: reaction pressure of 0.05-2 MPa, temperature of 400-750° C., and volumetric space velocity of 100-50,000 $h^{-1}$, preferably 800-8,000 $h^{-1}$. Because the aromatization catalyst has a high level of regenerability, the reaction temperature may be higher than that of the existing method. The reaction temperature in the present disclosure is preferably within a range of 600-750° C., such as 600° C., 610° C., 620° C., 630° C., 640° C., 650° C., 700° C., 750° C. or any temperature therebetween.

The method of the present disclosure can improve the yield of the target product—aromatic hydrocarbons, and the regenerated catalyst can still maintain high catalytic performance. In addition, the method of the present disclosure can meet the requirements of industrial application at the same time.

The present disclosure will be described below in detail with reference to examples.

In the following Preparation Examples and Comparative Preparation Examples, the colloidal silica is purchased from Sigma-Aldrich Incorporation under the product name Ludox AS-40;

The fumed silica is purchased from Sigma-Aldrich Incorporation;

The silicon carbide is commercially available from Sigma-Aldrich Incorporation;

$Al_2O_3$ is purchased from Sasol Company under the product name Catapal B;

The ZSM-5 zeolite powder (H-type ZSM-5) has a silica-alumina ratio of 30 and is commercially available from Sigma-Aldrich Incorporation;

The content of metal active components in the catalyst is measured according to the Inductively Coupled Plasma (ICP) method;

The content of zeolite (molecular sieve)=the use amount of zeolite/the sum amount of the inputted zeolite and binder;

The STEM elemental mapping is detected by using a transmission electron microscope (TEM, model number ARM200F) from the JEOL company.

Preparation Example 1

The ZSM-5 zeolite powder is mixed with an aqueous solution of $Pt(NO_3)_2$ having a concentration of 0.05 wt. %. The mixture is impregnated at room temperature for 1 hour, and then heated to 80° C. in a rotary evaporator to obtain a dried product, and subsequently subjected to calcinating at a temperature of 300° C. for 3 hours. The obtained calcinated product is mixed with $Al_2O_3$ according to a weight ratio of 70:30 and extruded for molding, and calcinated at a temperature of 550° C. for 2 hours. The catalyst is expressed as catalyst A and contains 500 ppm of Pt.

As can be seen from the STEM elemental mapping, 90 wt. % of Pt is distributed on the zeolite, a ratio of this percentage content to the percentage content of zeolite in the carrier is 90 wt. %/70 wt. %=1.29.

Comparative Preparation Example 1

The $Al_2O_3$ powder is mixed with an aqueous solution of $Pt(NO_3)_2$ having a concentration of 0.05 wt. %. The mixture is impregnated at room temperature for 1 hour, and then heated to 80° C. in a rotary evaporator to obtain a dried product, and subsequently subjected to calcinating at a temperature of 550° C. for 3 hours. The obtained calcinated product is mixed with ZSM-5 zeolite powder at a weight ratio of 30:70 and extruded for molding, and calcinated at a temperature of 550° C. for 2 hours, and pulverized and sieved to obtain particles of 20-40 mesh. The catalyst is expressed as catalyst B and contains 500 ppm of Pt.

As can be seen from the STEM elemental mapping, only 5 wt. % of Pt is distributed on the zeolite, a ratio of this percentage content to the percentage content of zeolite in the carrier is 5 wt. %/70 wt. %=0.07.

Comparative Preparation Example 2

The $Al_2O_3$ powder is mixed with an aqueous solution of $Pt(NO_3)_2$ having a concentration of 0.05 wt. %. The mixture is impregnated at room temperature for 1 hour, and then heated to 80° C. in a rotary evaporator to obtain a dried product, and subsequently subjected to calcinating at a temperature of 550° C. for 3 hours, the obtained calcinated product is compressed for molding, and pulverized and sieved to obtain particles of 20-40 mesh. The catalyst is expressed as catalyst C and contains 500 ppm of Pt.

Preparation Example 2

The ZSM-5 zeolite powder is mixed with $Al_2O_3$ at a weight ratio of 70:30 and extruded for molding, and then calcinated at a temperature of 550° C. for 2 hours, the obtained calcinated product is subjected to an ion exchange with an aqueous solution of $Pt(NO_3)_2$ having a concentration of 0.05 wt. % (the volumetric ratio of the calcinated product and the solution is 1:5), and the mixture is stirred at a temperature of 35° C. for 2 hours, and then subjected to a solid-liquid separation. The obtained product is washed with water to remove ions $Pt^{2+}$ physically adsorbed on ZSM-5 zeolite powder and $Al_2O_3$. Finally, the ion exchange product is dried overnight (8 hours) in air at a temperature of 90° C., and then calcinated at a temperature of 550° C. for 3 hours to prepare a catalyst. The catalyst is expressed as catalyst D and contains 500 ppm of Pt.

As can be seen from the STEM elemental mapping, 85 wt. % of Pt is distributed on the molecular sieve formed by the zeolite, a ratio of this percentage content to the percentage content of zeolite in the carrier is 85 wt. %/70 wt. %=1.21.

Comparative Preparation Example 3

The ZSM-5 zeolite powder is mixed with $Al_2O_3$ at a weight ratio of 70:30 and extruded for molding, and then calcinated at a temperature of 550° C. for 2 hours, the obtained particles are mixed with an aqueous solution of $Pt(NO_3)_2$ having a concentration of 0.05 wt. %, the obtained mixture is impregnated at room temperature for 1 hours, and then heated to 80° C. in a rotary evaporator to obtain a dried product, and subsequently subjected to calcinating at a temperature of 550° C. for 3 hours to prepare a catalyst. The catalyst is expressed as catalyst E and contains 500 ppm of Pt.

As can be seen from the STEM elemental mapping, 50 wt. % of Pt is distributed on the zeolite, a ratio of this percentage content to the percentage content of zeolite in the carrier is 50 wt. %/70 wt. %=0.71.

Preparation Example 3

The ZSM-5 zeolite powder is mixed with colloidal silica and fumed silica at a weight ratio of 70:20:10 and dried for molding, and then calcinated at a temperature of 550° C. for 2 hours, and pulverized and sieved to obtain particles of 20-40 mesh; the obtained particles are subsequently mixed with an aqueous solution of $Pt(NO_3)_2$ having a concentration of 0.05 wt. %, the obtained mixture is impregnated at room temperature for 1 hours, and then heated to 80° C. in a rotary evaporator to obtain a dried product, and subsequently subjected to calcinating at a temperature of 550° C. for 3 hours to prepare a catalyst. The catalyst is expressed as catalyst F and contains 500 ppm of Pt.

As can be seen from the STEM elemental mapping, 85 wt. % of Pt is distributed on the zeolite, a ratio of this percentage content to the percentage content of zeolite in the carrier is 85 wt. %/70 wt. %=1.21.

Preparation Example 4

The catalyst is prepared according to the method recited in Preparation Example 3, the only difference is the colloidal silica and fumed silica are replaced with silicon carbide, thereby obtaining a catalyst. The catalyst is expressed as catalyst G and contains 500 ppm of Pt.

As can be seen from the STEM elemental mapping, 90 wt. % of Pt is distributed on the zeolite, a ratio of this percentage content to the percentage content of zeolite in the carrier is 90 wt. %/70 wt. %=1.29.

Preparation Example 5

The ZSM-5 zeolite powder is mixed with an aqueous solution of $Pt(NO_3)_2$ having a concentration of 0.05 wt. %, the mixture is impregnated at room temperature for 1 hour, and then heated to 80° C. in a rotary evaporator to obtain a dried product, and subsequently subjected to calcinating at a temperature of 300° C. for 3 hours. The obtained calcinated product is then impregnated at room temperature in an aqueous solution of $Fe(NO_3)_3$ with a concentration of 0.1 wt. % for 1 hour, and then heated to 80° C. in a rotary evaporator for drying, and subsequently subjected to calcinating at a temperature of 300° C. for 2 hours. The calcinated product is mixed with $Al_2O_3$ at a weight ratio of 70:30 and extruded for molding, and calcinated at a temperature of 550° C. for 2 hours, and pulverized and sieved to obtain particles of 20-40 mesh. The catalyst is expressed as catalyst H and contains 400 ppm of Pt and 100 ppm of Fe.

As can be seen from the STEM elemental mapping, 90 wt. % of Pt and Fe are distributed on the zeolite, a ratio of this percentage content to the percentage content of zeolite in the carrier is 90 wt. %/70 wt. %=1.29.

Examples 1-5 and Comparative Example 1-3

The Examples 1-5 and Comparative Examples 1-3 are used for illustrating the method for aromatization of light alkanes according to the present disclosure and evaluating performance of the catalysts A-H and regenerated catalysts thereof respectively.

The regenerated catalysts are obtained by calcinating catalysts A-H (deposited with cokes after reacting for a period of time) at a temperature of 550° C. for 2 hours.

The specific evaluation methods are as follows:

1) Putting 1.0 g of catalyst into a quartz reactor (having an inner diameter of 9 mm);

2) Under 0.1 MPa of pressure, introducing 66.7 sccm of $H_2$ into the reactor and heating the reactor to 630° C. at a temperature rise rate of 15° C./min, and then maintaining the temperature at 630° C. for 30 minutes;

3) Replacing $H_2$ with 16.7 sccm ethane (with a volumetric space velocity of 1000 $h^{-1}$) and 3.0 sccm $N_2$ ($N_2$ is used as the interior label for chromatographic analysis); after 10 minutes of reaction, analyzing the product by an online gas chromatography every 35 minutes, and thereby calculating the ethane conversion and BTX selectivity.

Wherein

① The ethane conversion is calculated according to Equation 1:

Ethane conversion=(total molar amount of ethane−remaining molar amount of ethane)/total molar amount of ethane×100%     Equation 1

② The BTX selectivity is calculated according to Equation 2:

BTX selectivity=mole number of total carbon of BTX in the product/mole number of carbon in the converted ethane×100%     Equation 2

The catalytic performance of the aforementioned reactor after a certain period of time is shown in Table 1.

TABLE 1

| No. | Catalyst | Catalytic performance before regeneration [1] | | Run time before regeneration (minutes) | Catalytic performance after regeneration [2] | |
|---|---|---|---|---|---|---|
| | | Ethane conversion (%) | BTX selectivity (%) | | Ethane conversion (%) | BTX selectivity (%) |
| Example 1 | A | 55 | 50 | 250 | 54 | 51 |
| Comparative Example 1 | B | 18 | 42 | 230 | 18 | 43 |
| Comparative Example 2 | C | 20 | 1.1 | 150 | 19 | 0.5 |
| Example 2 | D | 57 | 48 | 180 | 56 | 50 |
| Comparative Example 3 | E | 58 | 48 | 80 | 40 | 50 |
| Example 3 | F | 60 | 55 | 230 | 60 | 57 |
| Example 4 | G | 58 | 52 | 230 | 55 | 50 |
| Example 5 | H | 55 | 59 | 240 | 55 | 60 |

1: The catalytic performance before regeneration refers to the catalytic performance when the catalyst is operated online for 80 minutes;

2: The catalytic performance after regeneration refers to the catalytic performance when the regenerated catalyst is operated online for 80 minutes.

As illustrated in the results of Table 1, the catalysts of the present disclosure have an advantage that the synergistic effect between the acid provided by the zeolite and the adjacent Pt not only leads to a high BTX selectivity, but also achieves a higher ethane conversion.

By comparing Example 1 and Comparative Example 1, it can be discovered that catalyst A exhibits higher activity (ethane conversion) and BTX selectivity than catalyst B.

It is illustrated in Comparative Example 2 that by removing zeolite from catalyst B, the prepared catalyst C shows a similar ethane conversion as catalyst B, but only a trace amount of BTX is discovered in the product. As can be seen, catalyst C can merely catalyze a dehydrogenation reaction (as dominant reaction) of ethane, and can't catalyze an aromatization reaction.

By comparing Example 2 with Comparative Example 3, it can be discovered that catalyst D introducing Pt by means of ion-exchange shows superior regeneration effect than catalyst E introducing Pt by means of impregnation, in the case that the zeolite and the binder $Al_2O_3$ are initially molded.

By comparing Example 3 with Comparative Example 3, it can be discovered that the catalyst F using the binder $SiO_2$ shows higher activity, BTX selectivity and regenerability, in the case that the zeolite and binder are initially molded for preparing a carrier, and the active component is subsequently impregnated.

The above content specifies the preferred embodiments of the present invention, but the present invention is not limited thereto. A variety of simple modifications can be made in regard to the technical solutions of the present invention within the scope of the technical concept of the invention, including a combination of individual technical features in any other suitable manner, such simple modifications and combinations thereof shall also be regarded as the content disclosed by the present invention, each of them falls into the protection scope of the invention.

The invention claimed is:

1. A method with increased the BTX selectivity and ethane conversion for aromatization of light alkanes, comprising:
   subjecting the light alkanes to a dehydroaromatization reaction in the presence of an aromatization catalyst comprising a carrier and a metal active component, the carrier comprising a zeolite and a binder, the metal active component comprising platinum at concentration of 400-10,000 ppm based on the total weight of the aromatization catalyst;
   regenerating the aromatization catalyst; and
   subjecting the light alkanes to a second dehydroaromatization reaction in the presence of the regenerated aromatization catalyst,
   wherein at least 80 wt. % of the metal active component is distributed on the zeolite.

2. The method of claim 1, wherein conditions of the dehydroaromatization reaction include: a reaction pressure of 0.05-2 MPa, a temperature of 400-750° C.; and a volumetric space velocity of 100-50,000 $h^{-1}$.

3. The method of claim 1, wherein conditions of the dehydroaromatization reaction include: a temperature of 600-750° C.; and a volumetric space velocity of 800-8,000 $h^{-1}$.

4. The method of claim 1, wherein the light alkanes are C2-C6 alkanes.

5. The method of claim 1, wherein the light alkanes are ethane.

6. The method of claim 1, wherein the zeolite is one or two or more selected from the group consisting of MFI, MEL, MTW, MOR, BEA, TMN and IMF zeolite.

7. The method of claim 6, wherein a silica-alumina ratio of the zeolite is within a range of 20-100.

8. The method of claim 1, wherein the platinum concentration is 500-5,000 ppm based on a total weight of the aromatization catalyst.

9. The method of claim 1, wherein content of the binder is 10-50 wt. % based on a total weight of the aromatization catalyst.

10. The method of claim 1, wherein content of the binder is 15-40 wt.% based on a total weight of the aromatization catalyst.

11. The method of claim 1, wherein weight percentage of the metal active component distributed on the zeolite based on a total amount of the metal active component is defined as P1, weight percentage of the zeolite in the carrier is defined as P2, and P1/P2 is higher than 1.1.

12. The method of claim 1, wherein the binder is one or two or more selected from the group consisting of alumina, lanthanum oxide, cerium oxide, zirconia and titanium dioxide.

13. The method of claim 12, wherein the aromatization catalyst is prepared with a method including the following steps:
1) molding
mixing the zeolite with the binder, molding and calcinating resulted mixture;
2) supporting
depositing ions of metal active component on calcinated product obtained in step 1) by an ion exchange method, and then drying and calcinating deposited product.

14. The method of claim 13, wherein the ion exchange in step 2) comprises: mixing and stirring a solution of compounds containing the metal active component with the calcinated products, and then sequentially performing solid-liquid separation and washing; the volumetric ratio of the solution and the calcinated products is within a range of 1-50:1, a temperature of stirring is 15-95° C., and the time of stirring is 0.5-10 hours.

15. The method of claim 1, wherein the binder is one or two or more selected from the group consisting of silica, aluminum phosphate and silicon carbide.

16. The method of claim 15, wherein the aromatization catalyst is prepared with a method including the following steps:
1) molding
mixing the zeolite with the binder, molding and calcinating resulted mixture;
2) supporting
supporting the metal active component on calcinated product obtained in step 1) by an impregnation method or an ion exchange method.

17. The method of claim 1, wherein the aromatization catalyst is prepared by a method including the following steps:
1) supporting
supporting the metal active component on the zeolites by an impregnation method or an ion exchange method;
2) molding
mixing a product obtained in step 1) with the binder, molding and calcinating resulted mixture.

18. The method of claim 1, wherein the metal active component further comprises iron.

19. The method of claim 5, wherein the dehydroaromatization reaction has a BTX selectivity of at least 50%.

20. The method of claim 19, wherein the dehydroaromatization reaction has an ethane conversion of at least 54%.

21. A method for aromatization of light alkanes, comprising:
subjecting the light alkanes to a dehydroaromatization reaction in the presence of an aromatization catalyst and at a temperature of 650° C.-750° C., the aromatization catalyst comprising a carrier and a metal active component, the carrier comprising a zeolite and a binder, and the metal active component comprising platinum at concentration of 500-10,000 ppm based on the total weight of the aromatization catalyst;
regenerating the aromatization catalyst and
subjecting the light alkanes to a second dehydroaromatization reaction in the presence of the regenerated aromatization catalyst, wherein
at least 80 wt. % of the metal active component is distributed on the zeolite.

22. The method of claim 21, wherein the metal active component further comprises iron.

23. The method of claim 21, wherein the metal active component consists essentially of platinum.

* * * * *

UNITED STATES PATENT AND TRADEMARK OFFICE
CERTIFICATE OF CORRECTION

PATENT NO. : 11,479,519 B2  
APPLICATION NO. : 16/728654  
DATED : October 25, 2022  
INVENTOR(S) : Hui Wang et al.

Page 1 of 1

It is certified that error appears in the above-identified patent and that said Letters Patent is hereby corrected as shown below:

On the Title Page

(73) Assignees should read:  
China Energy Investment Corporation Limited, Beijing, CN  
National Institute of Clean-and-Low-Carbon Energy, Beijing, CN Signed and Sealed this  
Ninth Day of July, 2024

Katherine Kelly Vidal  
*Director of the United States Patent and Trademark Office*